(12) United States Patent
Chen et al.

(10) Patent No.: US 9,302,259 B2
(45) Date of Patent: Apr. 5, 2016

(54) SOLID BASE CATALYST AND METHOD FOR MAKING AND USING THE SAME

(71) Applicant: Jiangsu Sinorgchem Technology Co., Ltd., Taizhou, Jiangsu Province (CN)

(72) Inventors: Xinmin Chen, Shanghai (CN); Jianliang Zhu, Nanjing (CN)

(73) Assignee: Jiangsu Sinorgchem Technology Co., Ltd., Taizhou, Jiangsu Province (CN)

( * ) Notice: Subject to any disclaimer, the term of this patent is extended or adjusted under 35 U.S.C. 154(b) by 338 days.

(21) Appl. No.: 13/684,136

(22) Filed: Nov. 21, 2012

(65) Prior Publication Data

US 2013/0079560 A1 Mar. 28, 2013

Related U.S. Application Data

(63) Continuation-in-part of application No. PCT/CN2011/074599, filed on May 24, 2011.

(30) Foreign Application Priority Data

May 24, 2010 (CN) .......................... 2010 1 0187702

(51) Int. Cl.
| | | |
|---|---|---|
| *B01J 31/26* | (2006.01) | |
| *C07C 209/38* | (2006.01) | |
| *C07C 209/26* | (2006.01) | |
| *B01J 31/06* | (2006.01) | |
| *B01J 23/04* | (2006.01) | |
| *B01J 31/02* | (2006.01) | |
| *B01J 31/08* | (2006.01) | |
| *C07C 209/36* | (2006.01) | |
| *C07C 209/60* | (2006.01) | |
| *B01J 31/00* | (2006.01) | |
| *B01J 37/02* | (2006.01) | |

(52) U.S. Cl.
CPC ........ *B01J 31/26* (2013.01); *B01J 23/04* (2013.01); *B01J 31/00* (2013.01); *B01J 31/0237* (2013.01); *B01J 31/0239* (2013.01); *B01J 31/0254* (2013.01); *B01J 31/0271* (2013.01); *B01J 31/06* (2013.01); *B01J 31/08* (2013.01); *B01J 37/0209* (2013.01); *C07C 209/26* (2013.01); *C07C 209/36* (2013.01); *C07C 209/38* (2013.01); *C07C 209/60* (2013.01)

(58) Field of Classification Search
None
See application file for complete search history.

(56) References Cited

U.S. PATENT DOCUMENTS

| | | |
|---|---|---|
| 2,635,100 A | 4/1953 | Werntz |
| 3,768,539 A | 10/1973 | Chamberline et al. |
| 3,797,552 A | 3/1974 | Frank et al. |
| 3,875,988 A | 4/1975 | Machida et al. |
| 3,896,057 A | 7/1975 | Lindsay et al. |
| 4,072,713 A | 2/1978 | Bjornson |
| 4,094,734 A | 6/1978 | Henderson |
| 4,102,926 A | 7/1978 | Usvyatsov et al. |
| 4,135,567 A | 1/1979 | Mattern |
| 4,178,315 A | 12/1979 | Zengel et al. |
| 4,187,248 A | 2/1980 | Merten et al. |
| 4,287,365 A | 9/1981 | Becker et al. |
| 4,313,002 A | 1/1982 | Symon et al. |
| 4,367,153 A | 1/1983 | Seiver et al. |
| 4,404,401 A | 9/1983 | Zengel et al. |
| 4,614,817 A | 9/1986 | Maender et al. |
| 4,683,332 A | 7/1987 | Sturm |
| 4,714,530 A | 12/1987 | Hale et al. |
| 4,760,186 A | 7/1988 | Solodar |
| 4,764,254 A | 8/1988 | Rosenblad |
| 4,776,929 A | 10/1988 | Aoyama et al. |
| 4,792,626 A | 12/1988 | Becher et al. |
| 4,900,868 A | 2/1990 | Merten et al. |
| 5,117,063 A | 5/1992 | Stern et al. |
| 5,118,388 A | 6/1992 | Aboul-Nasr |
| 5,253,737 A | 10/1993 | Klaue |
| 5,331,099 A | 7/1994 | Stern et al. |
| 5,420,354 A | 5/1995 | Malz et al. |
| 5,438,034 A | 8/1995 | Walker |
| 5,451,702 A | 9/1995 | Stern et al. |
| 5,453,541 A | 9/1995 | Stern et al. |
| 5,523,487 A | 6/1996 | Waler |
| 5,552,531 A | 9/1996 | Stern et al. |
| 5,554,573 A | 9/1996 | Cordier et al. |
| 5,608,111 A | 3/1997 | Stern et al. |
| 5,633,407 A | 5/1997 | Stern et al. |
| 5,739,403 A | 4/1998 | Reinartz et al. |
| 5,840,982 A | 11/1998 | Reynolds et al. |
| 5,925,791 A | 7/1999 | Buysch et al. |
| 5,932,768 A | 8/1999 | Ooms et al. |
| 5,973,206 A | 10/1999 | Laitinen |

(Continued)

FOREIGN PATENT DOCUMENTS

| | | | | |
|---|---|---|---|---|
| CN | 1721391 A | | 1/2006 | |
| CN | 101270037 A | * | 9/2008 | ............ C07C 47/565 |

(Continued)

OTHER PUBLICATIONS

Wohl, A., Chemische Berichte 34:2442-2450 (1901).
Wohl, A., Chemische Berichte 36:4135-4138 (1903).
Fan, "4-Nitrosodiphenylamine," Organic Synthetic Dictionary, Beijing University of Science and Engineering Publication House, (Oct. 2003).
Wei et al., "New Method for Making p-Nitrodiphenylamine," Chemical Report, No. 10 (1996).
Zhu et al., "Study on Hydrogenation of Nitrodyphenylamine in Alkalescence System," Journal of Nanjing University of Technology, vol. 24, No. 6, pp. 48-51 (Nov. 2002).
Stern et al., "Direct Coupling of Aniline and Nitrobenzene: A New Example of Nucleophilic Aromatic Substitution for Hydrogen," J. Am. Chem. Soc. 114:9237-9238 (1992).

(Continued)

*Primary Examiner* — Yun Qian

(74) *Attorney, Agent, or Firm* — Manni Li; Mei & Mark LLP

(57) ABSTRACT

A solid base catalyst having a carrier, an organic base, and an inorganic base. Both of the organic base and inorganic base are loaded on the carrier. The solid base catalyst is especially suitable for the synthesis of 4-Aminodiphenylamine (4-ADPA).

11 Claims, No Drawings

(56) References Cited

U.S. PATENT DOCUMENTS

| | | |
|---|---|---|
| 5,977,411 A | 11/1999 | DeVera |
| 5,985,231 A | 11/1999 | Filippi et al. |
| 5,994,584 A | 11/1999 | Ooms et al. |
| 6,043,394 A | 3/2000 | Langer et al. |
| 6,137,010 A | 10/2000 | Joo et al. |
| 6,140,538 A | 10/2000 | Rains et al. |
| 6,316,673 B2 | 11/2001 | Giera et al. |
| 6,365,745 B1 | 4/2002 | Matsui et al. |
| 6,368,996 B1 | 4/2002 | Mu et al. |
| 6,388,136 B1 | 5/2002 | Beska et al. |
| 6,395,933 B1 | 5/2002 | Triplett, II et al. |
| 6,395,934 B1 | 5/2002 | Wegener et al. |
| 6,403,852 B1 | 6/2002 | Yamamoto et al. |
| 6,414,192 B1 | 7/2002 | Schelhaas et al. |
| 6,423,872 B2 | 7/2002 | Marion |
| 6,495,723 B1 * | 12/2002 | DeVera et al. ............... 564/419 |
| 6,583,320 B2 | 6/2003 | Triplett, II et al. |
| 6,656,327 B2 | 12/2003 | Salmisuo |
| 6,680,280 B1 | 1/2004 | Birke et al. |
| 7,084,302 B2 | 8/2006 | Feng et al. |
| 7,112,262 B2 | 9/2006 | Bethge |
| 7,157,605 B2 | 1/2007 | Kim et al. |
| 7,176,333 B2 | 2/2007 | Wang et al. |
| 7,189,684 B2 | 3/2007 | Ohno et al. |
| 7,235,694 B2 | 6/2007 | Feng et al. |
| 7,989,662 B2 | 8/2011 | Feng et al. |
| 8,293,673 B2 | 10/2012 | Feng et al. |
| 8,486,223 B2 | 7/2013 | Feng et al. |
| 8,686,188 B2 | 4/2014 | Feng et al. |
| 2001/0025798 A1 | 10/2001 | Andolfatto |
| 2002/0055652 A1 | 5/2002 | Schelhaas et al. |
| 2003/0088127 A1 | 5/2003 | Triplett et al. |
| 2006/0258887 A1 | 11/2006 | Kim et al. |
| 2009/0048465 A1 | 2/2009 | Feng et al. |
| 2013/0066113 A1 | 3/2013 | Feng et al. |

FOREIGN PATENT DOCUMENTS

| | | |
|---|---|---|
| EP | 0148145 A1 | 7/1985 |
| EP | 184914 | 6/1986 |
| EP | 0566783 A1 | 10/1993 |
| EP | 0734765 A1 | 10/1996 |
| GB | 947082 | 1/1964 |
| GB | 1198508 A | 7/1970 |
| GB | 2015998 A | 9/1979 |
| JP | 62-062814 A | 3/1987 |
| JP | H06306020 A | 11/1994 |
| JP | H06306021 A | 11/1994 |
| JP | 2002249467 A | 9/2002 |

OTHER PUBLICATIONS

Stern et al., "Eliminating Chlorine in the Synthesis of Aromatic Amines: New Routes Which Utilize Nucleophilic Aromatic Substitution for Hydrogen," New J. Chem. 20:259-268 (1996).

Stern, "Chap. 11, Nucleophilic Aromatic Substitution of Hydrogen," ACS Symposium Series 577, Benign by Design (Aug. 1993).

Dickneider, "A Green Chemistry Module," website printout of Nov. 2003, http://academic.scranton.edu/faculty/CANNM1/advancedorganic/advancedorganicmodule.htm.

M. Makosza, "Phase transfer catalysis. A general green methodology in organic synthesis," Pure Appl. Chem., vol. 72, No. 7, pp. 1399-1403 (2000).

Dai, Yanfeng et al., "Preparation for High Quality Tetrapropyl Ammonium Hydroxide,"Specialty Petrochemicals, vol. 2, pp. 28-30 (Mar. 1998).

Zhang, Zhongmin et al., "Research on Preparation of Tetramethyl Ammonium Hydroxide by Electrolysis," Jiangxi Chemical Engeering, vol. 2, pp. 11-14 (1996).

Goldman, "Activation of Manganese Dioxide by Azeotropic Removal of Water," J. Org. Chem., 1969, vol. 34, No. 6, pp. 1979-1981 (Jun. 1969).

Anonymously, Research Disclosure, Research Disclosure Database, No. 407033, published in the Mar. 1998 Paper journal.

* cited by examiner

SOLID BASE CATALYST AND METHOD FOR MAKING AND USING THE SAME

CROSS-REFERENCE AND RELATED APPLICATIONS

The subject application is a continuation-in-part of PCT international application PCT/CN2011/074599 filed on May 24, 2011, which in turn claims priority on Chinese patent application No. CN 201010187702.7 filed on May 24, 2010. The contents and subject matter of all the priority applications are incorporated herein by reference.

FIELD OF THE INVENTION

The subject application relates to a catalyst, and in particular, a solid base catalyst, and method for making and using the same.

BACKGROUND OF THE INVENTION

4-Aminodiphenylamine (4-ADPA) is an intermediate for making paraphenylenediamines (PPDs) which are anti-degradants for various polymers including rubbers. 4-ADPA can be produced in various ways. First, 4-ADPA can be produced by reacting p-chloronitrobenzene with an aniline derivative in the presence of an acid acceptor to produce 4-nitrophenylamine, followed by the reduction of the nitro group. See, for examples, U.S. Pat. Nos. 4,187,248 and 4,683,332. Second, 4-ADPA can be produced by the hydrogenation of p-nitrodiphenylhydroxylamine. See, for examples, U.S. Pat. Nos. 4,178,315 and 4,404,401. Third, 4-ADPA can be produced by the head-to-tail coupling of aniline. See, for example, U.S. Pat. No. 4,760,186. Fourth, 4-ADPA can be produced by reacting acetanilide and nitrobenzene in DMSO to make nitrosodiphenylamine, followed by the reduction of the nitrosodiphenylamine. Fifth, 4-ADPA can be produced by a one-step reaction in which nitrobenzene is contacted with hydrogen and react with aniline in the presence of a hydrogenation catalyst, a hydrogenation inhibitor, and an acid catalyst. Sixth and currently the preferred reaction route for the commercial production of 4-ADPA, aniline and nitrobenzene are condensed to produce 4-nitrosodiphenylamine (4-NODPA) and 4-nitrodiphenylamine (4-NDPA) which are then hydrogenated to produce 4-ADPA. See, for examples, U.S. Pat. Nos. 5,117,063 and 5,453,541.

In the currently preferred process, the condensation reaction of nitrobenzene and aniline to produce 4-NOPDA and 4-NDPA are conducted in the presence of the phase transfer catalyst, typically tetramethyl ammonium hydroxide (TMAH), which is also used as an organic base. In the process, a small amount of azobenzene, phenazine, and other by-products are produced. 4-NDPA and 4-NODPA are then catalytically hydrogenated to produce 4-ADPA.

The current process requires a large amount of the organic base in the aqueous solution as the catalyst. The catalyst may be closely bound to the reaction products, 4-NDPA and 4-NODPA, after the condensation reaction, and thus, cannot be separated from the reaction products and regenerated in situ. The catalyst can only be released after the 4-NDPA and 4-NODPA have been hydrogenated to 4-ADPA, therefore, must go through the hydrogenation reaction. The catalyst is somewhat unstable, and often decomposes during the hydrogenation and subsequent concentration and recycle steps. Higher temperature, longer reaction time, and larger amount used lead to even greater decomposition of the catalyst.

The current process for producing 4-ADPA using water-soluble phase transfer catalysts also consumes a large amount of energy to protect and recycle the catalyst. The condensation of aniline and nitrobenzene requires low water content. While the organic base catalyst utilized in the condensation reaction can be extracted after the hydrogenation reaction, the concentration of the catalyst in the water phase extracted is low. It is even lower in the reaction system after the addition of methanol for separating the organic and aqueous phases. In order to recycle and reuse the organic base catalyst, it must be concentrated, which requires the use of additional energy.

Furthermore, the current production process for producing 4-ADPA from aniline and nitrobenzene may be unstable. Impurities are formed due to the continuous decomposition and reaction of the condensation catalyst during the subsequent steps before the catalyst can be recycled, which reduce efficiency and impede production. The reaction conditions are continuously changing as these impurities mount thereby altering the reaction conditions for condensation, hydrogenation, and especially phase separation. Thus, the process of producing 4-ADPA becomes less predictable and controllable.

The current process for producing 4-ADPA requires stringent conditions for performing the hydrogenation reaction which ultimately slows the production. For example, in order to prevent the condensation catalyst from decomposing during the hydrogenation reaction, the temperature of the hydrogenation reaction must be limited to 90° C. or lower. As a result, a hydrogenation catalyst with high activity at low temperature must be used, usually a noble metal catalyst. Noble metal catalysts are expensive and often require an organic solvent to accelerate the reaction. Such solvents will ultimately need to be recovered from the reaction system thereby increasing energy costs.

U.S. Pat. No. 6,395,933 describes a process for making 4-ADPA by reacting nitrobenzene and substituted aniline at a controlled temperature in the presence of a strong base and a phase transfer catalyst. The process results in low yields and increased side reactions. The process is costly and also requires an oxidizing agent which makes it unsuitable for the commercial production.

U.S. Pat. No. 6,495,723 describes a composition for use in the condensation of aniline and nitrobenzene which is composed of a solid carrier, typically zeolite, having interior channels containing a base. The cross-sectional dimensions of the channels provide an environment that improves the selectivity of the reaction such that undesired by-products such as phenazine or azobenzene are limited. The internal diameter of the zeolite carrier described in the patent is quite small such that the interior channels of that carrier are quite restrictive. Because of the limited utilization of interior surface, any attempted regeneration reaction of the organic catalyst would be mainly carried out on exterior surface. Furthermore, the small diameter of the zeolite internal channels prevents high loading values for the organic catalyst. As such, more catalyst would need to be added to a condensation reaction in order to maintain high catalytic activity and industrial value.

U.S. Patent Publication No. 2009/0048465 describes a complex base catalyst comprised of tetraalkyl ammonium hydroxide, an alkali metal hydroxide or oxide, and a tetraalkyl ammonium salt in the aqueous form that reduces the need to tightly control the quantity of protic materials in the condensation reaction. The complex base catalyst also decreases the conversion of tetraalkyl ammonium hydroxide to tetraalkyl ammonium carbonate thereby reducing the need to replenish the catalyst during the reaction. However, the complex base catalyst is not in a solid phase and therefore still must be separated, regenerated, and recycled.

Thus, in the condensation reaction of aniline and nitrobenzene, the current process for producing 4-ADPA using organic base catalyst requires a large amount of the catalyst and need to recycle the catalyst after several reaction steps. The current process can not be completed rapidly, and can also consume high energy. The current process requires increased solvent usage and more solvent recycle steps are needed, thus, the impurities will increase which lead to the decrease in efficiency and quality of the 4-ADPA production process. Therefore, there is a need to overcome the disadvantages of the current process for producing 4-ADPA.

SUMMARY OF THE INVENTION

The subject application provides a novel catalyst for the production of 4-ADPA, which overcomes the defects of the current catalyst which are difficult to be recycled and easy to decompose.

The solid base catalyst of the subject application includes a carrier, an organic base, and an inorganic base. Both of the inorganic base and organic base are loaded on the carrier. The organic base serves to catalyze the condensation reaction, and the inorganic base serves to regenerate the organic base catalyst.

The carrier may be an inorganic carrier, such as alumina, silica, diatomite, molecular sieve, and macroporous resin, including the ion exchange resin, especially the strong basic ion exchange resin. The carrier owns many interior channels and an enormous interior surface such that condensation reactions can be carried out on the interior surface. The interior surface may be loaded with enough inorganic bases to regenerate the organic base without reducing the activity of the organic catalyst. In general, the carrier may be loaded with a higher amount of the catalyst. It enables the solid base catalyst of the subject application to maintain higher activity, and requires less catalyst for the condensation of the same amount of reactants as compared with catalyst loaded on zeolite.

The subject application further provides a method for making the solid base catalyst where the organic base is polymerized with the carrier to produce a carrier-containing organic base and then the carrier-containing organic base is reacted with an aqueous solution of the inorganic base to produce the solid base catalyst.

The present application also includes methods for making 4-ADPA where aniline and nitrobenzene are condensed in the presence of the solid base catalyst to produce 4-nitrosodiphenylamine and 4-nitrodiphenylamine which are subsequently hydrogenated to produce 4-aminodiphenylamine. During the method of synthesizing 4-ADPA using the process of the subject application, the solid base catalyst is regenerated and reused in situ, therefore, there is no need for a separate step to recycle the condensation catalyst.

The solid base catalyst of the present application need not be recovered, concentrated, or recycled, thereby the process for producing 4-ADPA is more efficient, predictable, faster, less costly, and more environmentally friendly. When the solid base catalyst of the present invention is used for producing 4-ADPA, the amount of the organic base catalyst used will be significantly reduced, and the air pollution caused by the decomposition of the organic base will be reduced. It has environmental benefits.

DETAILED DESCRIPTION OF THE INVENTION

The carrier in the solid base catalyst of the present invention may be an inorganic carrier, for examples, a polar inorganic carrier, such as activated alumina, porous silica, and diatomite. The carrier has a large specific surface area. Preferably, the total specific surface area of the carrier is about 800 to 1500 $m^2/g$. The carrier has a large amount of oxygen atoms loaded on its surface which may combine with organic or inorganic alkali well. During the process of making the catalyst and loading the organic base onto the carrier, the organic base reacts with the carrier to form chemical bonding, while the inorganic base is physically adsorbed in the carrier.

The carrier may also be a macroporous adsorption resin. Preferably, the resin is an anion exchange resin to which the organic base may be chemically bound during the loading process, while the inorganic base may be physically adsorbed in the networks of the carrier. Preferably, the resin has a particle size of about 0.1 mm to 5.0 mm in diameter, a density of about 0.3 g/ml to about 1.2 g/ml, and an exchange capacity of equal to or greater than about 1 mmol/g. The specific area of the resin is about 200 to about 1000 $m^2/g$, and the pore diameter is about 0.5 nm to about 500 nm, preferably about 0.8 nm to about 500 nm, and more preferably about 1.0 nm to about 500 nm. In one preferred embodiment of the present invention, the anion exchange resin is styrene base anion exchange resin.

The amount of the organic base that is bound on the carrier is about 1 to 20% weight percentage of the catalyst, and preferably, 10 to 18% weight percentage of the catalyst.

The amount of the inorganic base that is adsorbed on the carrier is about 0.5 to 25% weight percentage of the catalyst, and preferably, 5 to 10% weight percentage of the catalyst.

The solid base catalyst of the present invention comprises dual reactive groups which are used in the condensation reaction. One active group is the catalytic group for condensation which is the organic base that catalyzes the condensation of aniline and nitrobenzene. The organic base can be, but not limited to, methylamine, ethylamine, cyclohexylamine, and other fatty amines, aniline, phenyl diamine, and other aromatic amines, quaternary ammonium salts or alkali such as dodecyl trimethyl ammonium chloride, trimethyl benzyl ammonium chloride, tetramethyl ammonium chloride, tetramethyl ammonium bromide, tetraethyl ammonium hydroxide, tetrapropyl ammonium hydroxide, tetrabutyl ammonium hydroxide, tetramethyl ammonium hydroxide, benzyl trimethyl ammonium hydroxide, benzyl triethyl ammonium hydroxide, 4-dimethylamino pyridine and crown ethers which are phase transfer catalysts, or a mixture thereof. In a preferred embodiment of the present application, the organic base is a tetraalkyl ammonium hydroxide, preferably tetramethyl ammonium hydroxide or tetraethyl ammonium hydroxide.

The other active group is the regenerating group which comprises an inorganic base which regenerates the organic base. The inorganic base can be, but is not limited to, potassium hydroxide, sodium hydroxide, calcium hydroxide, cesium hydroxide, aluminum hydroxide, sodium methoxide, potassium methoxide, sodium ethoxide, and potassium ethoxide. Since the active component of the catalyst is fixed on a carrier, the heat resistance and anti-decomposition capacity are improved and its activity is more stable. In a preferred embodiment of the present application the regenerating inorganic base is sodium hydroxide or potassium hydroxide.

The solid base catalyst is used in the condensation reaction to effectively catalyze the condensation of aniline with nitrobenzene to produce the intermediates, 4-nitrosodiphenylamine and 4-nitrodiphenylamine as well as some other by-products such as azobenzene. 4-NDPA and 4-NODPA are then directly hydrogenated to produce 4-ADPA. By-products such as azobenzene and excess aniline are recycled and reused as pre-distillate. The amount of waste materials produced during the process with the use of the solid base catalysts of the present application is dramatically reduced.

Methods of making the solid base catalyst include polymerizing the organic base with a carrier to produce a carrier containing organic base. The carrier-containing organic base is then reacted with an aqueous solution of inorganic base to produce the solid base catalyst of the present application. In a preferred method of making the solid base catalyst, tetraethyl ammonium hydroxide is polymerized with styrene resin in the presence of water to produce styrene resin containing tetraethyl ammonium hydroxide. The styrene resin containing tetraethyl ammonium hydroxide is then reacted with an aqueous solution of potassium hydroxide to produce the solid base catalyst of the present application.

In one embodiment of the present invention, macroporous strong basic anion-exchange resins such as D201 and D202 are mixed with an aqueous solution of TMAH at 20-25 wt %. (The names of the resins are used in consistent with the designations of resins under the national standard in China, "National Standard for the "Designation System and Basis for Specifications Of Ion Exchange Resins (GBT 1631-2008)," which was promulgated on Jun. 30, 2008 and went into effect on Feb. 1, 2009 in China. The contents of the Chinese national standard is hereby incorporated by reference. According to the standard, D201 and D202 refer to macroporous type strong base resins in the styrene series.) The weight ratio of the macroporous strong basic anion-exchange resin to the TMAH aqueous solution is about 1:(0.1-10), preferably about 1:(0.5-5), and more preferably 1:(0.5-1.0). For example, to a 1000 ml four-necked flask equipped with a stirrer and a condenser, 200 g D201 resin and 400 g 25 wt % TMAH aqueous solution are added. While stifling, the mixture is heated and maintained at reflux at the temperature of approximately 50-100° C., preferably 70-90° C., and more preferably 70-80° C. The reflux reaction holds on for 5-8 hours, preferably 6-7 hours. The reaction mixture is transferred into a beaker when it cools down to room temperature. The resin containing TMAH is produced after filtration and washing by water. 200 g resin containing TMAH is put into a reaction flask, and 50 wt % aqueous solution of potassium hydroxide is added. Generally, the weight ratio of the resin to the aqueous solution of potassium hydroxide is about 1:(0.1-5), preferably 1:(0.5-1). The reaction mixture is stirred and maintained at 5-100° C., preferably at 10-50° C., and more preferably at 30-40° C. The reflux reaction holds on for 1-8 hours, preferably 2-3 hours. The mixture is then cooled. After filtration and washing by water, the wet solid base catalyst is heated slowly in the oven at less than 50° C. until dry. The dried solid base catalyst comprising the dual reactive groups is produced.

The condensation reaction of aniline and nitrobenzene can be carried out in a kettle-type reactor or tower or fluidized bed or fixed bed reactor in which the catalyst can be fixed or free flowing in the reaction mixture. The condensation reaction can be carried out under any pressure conditions including a vacuum, intermittent vacuum, atmospheric pressure or increased pressure. The condensation reaction can be carried out from about 0-105° C.

The use of an organic base as a catalyst in the condensation reaction between aniline and nitrobenzene produces intermediates such as 4-NDPA and 4-NDOPA which are complexed with the organic base catalyst. In the current methods of producing 4-ADPA the organic base is not released from the complex until the 4-NDPA and 4-NDOPA are hydrogenated to 4-ADPA. At this point the organic base is released and can be recycled. In the compositions and methods of the present application, the inorganic base that is part of the solid base catalyst reacts with the 4-NDPA and 4-NDOPA complexed to the organic base and releases the 4-NDPA and 4-NDOPA and organic base such that the organic base can catalyze another round of condensation between and aniline and nitrobenzene and the 4-NDPA and 4-NDOPA can subjected to a hydrogenation step to produce 4-ADPA.

Further, 4-ADPA can be reductively alkylated to make alkylated paraphenylenediamines by known methods. Preferably, 4-ADPA and a suitable ketone or aldehyde are reacted in the presence of hydrogen and a hydrogenation catalyst. Suitable ketones include methylisobutyl ketone (MIBK), acetone, methylisoamylketone, and 2-octanone. See, for examples, U.S. Pat. No. 4,900,868 and as depicted in WO 93/00324, at page 13, lines 12 to 24, the contents of which are incorporated herein by reference.

Thus, the organic base catalyst in the condensation reaction is continuously regenerated and condensation product is continuously released from the catalyst, thus the condensation catalyst can remain in the condensation reactor without being brought into the hydrogenation and phase separation steps, thereby improving the efficiency of the process as well as providing for better control and predictability of the synthesis of 4-ADPA.

On the other hand, due to the use of above carriers and a substantially anhydrous reaction condition (a small amount of water generated during reaction will be timely separated), the organic base and inorganic base loaded on the surface of the carriers are not easy to precipitate from the carriers. Thus, the solid base catalyst of the present application can be used repeatedly with well catalytic efficiency.

Since the organic base catalyst is no longer carried into the hydrogenation reaction, this reaction can be carried out in a wider temperature range and thereby permit different catalysts to be used under a variety of conditions which may increase the speed of the hydrogenation reaction. The absence of the organic base catalyst in the hydrogenation reaction also reduces the need for solvents. For example, without the presence of an organic base catalyst in the hydrogenation reaction, a nickel catalyst can be used at elevated temperatures 50°-140° C. without solvent.

Because the organic base catalyst is regenerated in the condensation reaction, there need be no recovery, concentration, or recycling of the catalyst. In addition, almost all of the raw materials used in the production of 4-ADPA are converted to desired products without production of unwanted by-products. The process is environmentally friendly. Other than a small amount of water generated during the condensation and hydrogenation reactions just a small amount of residual material is produced during the process. No other materials will be discharged including gas emission.

The process will require less energy consumption. In addition to maintaining the reaction temperature and necessary distillation and refining steps for product purification, no large quantity of materials need to be heated, recovered, or removed. If the heat generated in the hydrogenation reaction can be taken advantage of, the energy required for the entire process will be even less.

The present invention is further illustrated in the following examples. The examples show the embodiments of the invention and are not intended to limit the scope of protection of the invention. For those skilled in the art, variations and modifications can be made to the invention without departing from the scope of the invention.

Example 1

Making of Solid Base Catalyst

To a 1000 ml four-necked flask equipped with a stirrer and a condenser were added to 200 g D201 resin and 400 g 25 wt % TMAH aqueous solution. While stifling, the mixture was heated and maintained at reflux at the temperature of approximately 75° C. The reflux reaction holds on 6 hours. Put the reaction mixture aside after it is transferred into a beaker when it cools down to room temperature. The resin containing tetra methyl ammonium hydroxide is produced after filtration and wash by water. To a 500 ml three-necked flask equipped with a stirrer and a condenser were added to 200 g resin containing tetra methyl ammonium hydroxide and 200 ml 50 wt % aqueous solution of potassium hydroxide. While stirring, the mixture was heated and maintained at reflux at the temperature of approximately 50-100° C. for about 2 hours. The mixture was then cooled. After filtration, the wet solid base catalyst was heated slowly in the oven (less than 50° C., at 0.098MPA) until dry. The dried solid base catalyst was kept in the desiccator until use.

Example 2

Making of Solid Base Catalyst

To a 1000 ml four-necked flask equipped with a stirrer and a condenser were added to 300 g activated alumina (grain diameter 2-3 mm, produced by Pingxiang city Tianli Chemical fillings Limited company) and 400 g 25 wt % TMAH aqueous solution. While stifling, the mixture was heated and maintained at reflux at the temperature of approximately 75° C. The reflux reaction holds on 6 hours. Put the reaction mixture aside after it is transferred into a beaker when it cools down to room temperature. To a 500 ml three-necked flask equipped with a stirrer and a condenser were added to 200 g activated alumina containing tetra methyl ammonium hydroxide and 200 ml 50 wt % aqueous solution of potassium hydroxide. While stifling, the mixture was heated and maintained at reflux at the temperature of approximately 50-100° C. for about 2 hours. The mixture was then cooled. After filtration, the wet solid base catalyst was heated slowly in the oven (less than 50° C., at 0.098 MPA) until dry.

Example 3

Synthesis of 4-ADPA Using Catalyst

To a 500 ml three-necked flask equipped with a stirrer and a condenser were added 50 g solid base catalyst prepared according to example 1 and 150 ml aniline. The mixture was heated to 75° C. and the pressure was maintained at approximately 0.095 Mpa. When the temperature was controlled between 70-75° C., 50 ml nitrobenzene was added and the condensation reaction was begun. Water produced during the reaction was separated from the mixture. The nitrobenzene residue content was analyzed continuously after reacting for 10 h. The reaction was stopped when less than 1% nitrobenzene remained.

The reaction mixture was filtered to recycle the solid phase and yielded 280 ml of condensed liquid. Analysis of the liquid confirmed that the conversion of nitrobenzene was approximately 99%, and the content of 4-NDPA and 4-NDOPA was 18% based on condense liquid. A small amount of azobenzene and other by-products were produced in the reaction. The 280 ml condense liquid was diluted with 70 ml water and 5 wt % Raney nickel catalyst was added to a high pressure hydrogenation reactor. In order to ensure the absence of oxygen gas, hydrogen gas was passed into the reactor to replace the atmosphere inside. The reaction mixture was heated and the pressure was controlled at about 1.5 Mpa. The mixture was heated to about 60° C., and the stir was opened and the hydrogenation reaction was begun. The reaction temperature was maintained at 80-120° C. for 2 hours. The reaction stopped when no hydrogen gas was found to be absorbed.

After filtration, the Raney nickel catalyst was recycled. The water phase was separated from the mixture to give 260 ml of hydrogenation material. Chemical analysis revealed that the reaction conversion was 98%. The content of target product 4-ADPA was 20%. Small amount of by-products were produced.

The finished 4-ADPA product was obtained by distillation or refining after aniline and by-products were distilled from the hydrogenation material. The recycled aniline and by-products were reused.

Example 4

Synthesis of 4-ADPA Using Fixed Catalyst 50 g solid base catalyst prepared according to example 2 was packaged by 60 mesh net. The 4-ADPA was prepared under the reaction conditions of example 3. After the reaction, the solid catalyst was remained in the reactor.

280 ml condense liquid was produced by the reaction. Chemical analysis revealed that the conversion of nitrobenzene was 96%, the content of 4-NDPA and 4-NDOPA was 25% based on condensed liquid. A small amount of azobenzene and other by-products were produced in the reaction. Chemical analysis also revealed that reaction conversion was 98%. The content of target product RT-base was 20%. Small amount of by-products were produced.

Example 5

The catalyst prepared according to example 1 was repeatedly applied for 15 times under the reaction conditions of example 3, and then the nitrobenzene conversion rate of the fifteenth catalytic condensation reaction was still 98.5%.

Example 6

The catalyst prepared according to example 2 was repeatedly applied for 15 times under the reaction conditions of example 3, and then the nitrobenzene conversion rate of the fifteenth catalytic condensation reaction was 68%.

We claim:

1. A solid base catalyst comprising
an organic base,
an inorganic base; and
a carrier,
wherein the organic base is polymerized with the carrier, and the inorganic base is physically adsorbed in the carrier to regenerate the organic base in situ; and
the carrier is a macroporous strong basic anion-exchange styrene resin that is D201 or its equivalent Amberlite IRA900 resin having a matrix structure of a copolymerized styrene—DVB gel resin, a functional group of —$N^+(CH_3)_3$, an appearance of milky white opaque spherical particles, being shipped in a Cl-ionic form, having a strong group of capacity of equal to or more than 3.7 mmol/g when dry in the Cl-ionic form, a total exchange capacity in volume of equal to or more than 1.15 mmol/mL in the Cl-ionic form, a moisture holding capacity of 50-60% in the Cl-ionic form, a specific gravity of 1.06 g/mL to 1.10 g/mL in the Cl-ionic form, a shipping weight of 0.65 g/mL to 0.73 g/mL in the Cl-ionic form, a harmonic mean size of 0.40 mm to 0.70 mm, a particle size of 0.315 mm to 1.25 mm for equal to or more than 95% of the particles and less than 0.315 mm for less than 1% of the particles, a uniformity coefficient of equal to or less than 1.6, an osmotic-attrited of equal to or more than 90%, and a maximum reversible swelling of Cl—OH— at 25%.

2. The solid base catalyst of claim 1, wherein the organic base is methylamine, ethylamine, cyclohexylamine, aniline, phenyl diamine, dodecyl trimethyl ammonium chloride, trimethyl benzyl ammonium chloride, tetramethyl ammonium chloride, tetramethyl ammonium bromide, tetramethyl ammonium hydroxide, tetraethyl ammonium hydroxide, tetrapropyl ammonium hydroxide, tetrabutyl ammonium hydroxide, tetramethyl ammonium hydroxide, benzyl trimethyl ammonium hydroxide, benzyl triethyl ammonium hydroxide, 4-dimethylamino pyridine, crown ether, or a mixture thereof.

3. The solid base catalyst of claim 1, wherein the organic base is tetramethyl ammonium hydroxide or tetraethyl ammonium hydroxide.

4. The solid base catalyst of claim 1 wherein the inorganic base is potassium hydroxide, sodium hydroxide, calcium hydroxide, cesium hydroxide, aluminum hydroxide, sodium methoxide, sodium ethoxide, potassium methoxide, potassium ethoxide, or a mixture thereof.

5. The solid base catalyst of claim 1, wherein the inorganic base is potassium hydroxide or sodium hydroxide.

6. The solid base catalyst of claim 1, wherein an amount of the organic base that is loaded on the carrier is 1 to 20% weight percentage of the catalyst.

7. The solid catalyst of claim 1, wherein an amount of the inorganic base that is adsorbed on the carrier is 0.5 to 25% weight percentage of the catalyst.

8. A method for producing the solid base catalyst of claim 1, comprising
polymerizing the organic base with the carrier to produce a organic base-bound carrier, and
reacting the organic base-bound carrier with an aqueous solution of the inorganic base to produce the solid base catalyst.

9. A method for using the solid base catalyst of claim 1, comprising
condensing aniline and nitrobenzene in presence of the solid base catalyst to produce 4-nitrosodiphenylamine and 4-nitrodiphenylamine, and
hydrogenating the 4-nitrosodiphenylamine and 4-nitrodiphenylamine to produce 4-aminodiphenylamine.

10. The method of claim 9, wherein the solid base catalyst is regenerated in situ.

11. The method of claim 9, further comprising
reductively alkylating the 4-aminodiphenylamine with a suitable ketone or aldehyde in presence of hydrogen and a hydrogenation catalyst to make alkylated derivatives of 4-aminodiphenylamine.

* * * * *